United States Patent
Hashida et al.

(10) Patent No.: US 6,500,916 B1
(45) Date of Patent: Dec. 31, 2002

(54) CARRIER POLYMERS MIGRATING INTO TARGET ORGANS AND DRUG-CONTAINING POLYMERS

(75) Inventors: Mitsuru Hashida, Kyoto (JP); Ken Akamatsu, Hyogo (JP)

(73) Assignee: Ono Pharmaceutical Co., Ltd., Osaka (JP)

( * ) Notice: Subject to any disclaimer, the term of this patent is extended or adjusted under 35 U.S.C. 154(b) by 0 days.

(21) Appl. No.: 09/623,136

(22) PCT Filed: Mar. 2, 1999

(86) PCT No.: PCT/IB99/00361

§ 371 (c)(1),
(2), (4) Date: Aug. 28, 2000

(87) PCT Pub. No.: WO99/43736

PCT Pub. Date: Feb. 9, 1999

(30) Foreign Application Priority Data

Feb. 27, 1998 (JP) .......................................... 10-064833

(51) Int. Cl.$^7$ ................................................ C08G 69/10
(52) U.S. Cl. ....................... 528/328; 528/310; 528/486; 525/419; 525/420; 530/322; 530/345; 514/8
(58) Field of Search ................................ 530/345, 322; 514/8; 528/310, 328, 486; 525/419, 420

(56) References Cited

U.S. PATENT DOCUMENTS

| | | | | |
|---|---|---|---|---|
| 3,985,617 A | * | 10/1976 | Yugari | 195/68 |
| 4,371,673 A | * | 2/1983 | Pitha | 525/426 |
| 5,480,998 A | | 1/1996 | Hamanaka et al. | 546/333 |
| 5,650,270 A | * | 7/1997 | Giese | 435/6 |

FOREIGN PATENT DOCUMENTS

| | | | |
|---|---|---|---|
| JP | 7-228688 | 8/1995 | .......... C08G/69/10 |
| WO | 92/00748 | 1/1992 | .......... A61K/31/765 |

OTHER PUBLICATIONS

Akamatsu, K., et al, "Synthesis and biodistribution study of liver–specific prostaglandin E1 polymeric conjugate", International Journal of Pharmaceutics, p. 65–74, 1997.
Akamatsu, K., et al, "Synthesis and biodistribution study of liver–specific prostaglandin E1 polymeric conjugate", International Journal of Pharmaceutics, p. 65–74, 1997.

* cited by examiner

*Primary Examiner*—Christopher S. F. Low
*Assistant Examiner*—David Lukton
(74) *Attorney, Agent, or Firm*—Sughrue Mion, PLLC

(57) ABSTRACT

Polymers derived from polymers represented by Formula (A) (d is 20~500; and Rs, which may be the same or different, represent each H, alkyl or benzyl) by substituting a part or all of the consisting peptide bonds by (1) hydrazino-Glu (Formula B), and saccharide-modified Glu (Formula C) or by (2) hydorazino-Glu (Formula B), and saccharide-modified Glu (Formula C), and drug bonded Glu (Formula D). These polymers, which are carriers optionally bonded to drugs capable of migrating into target organs (cells), are useful as medicines

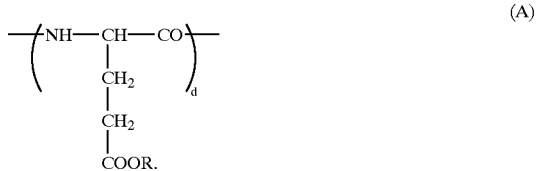

(A)

3 Claims, No Drawings

CARRIER POLYMERS MIGRATING INTO TARGET ORGANS AND DRUG-CONTAINING POLYMERS

THE FIELD OF THE ART

The present invention relates to saccharide-modified polymers which are useful as carriers capable of migrating into target organs (cells), drug-containing polymers using them and the process for the preparation thereof.

BACKGROUND

The drug delivery systems into the target organs comprising low-molecular drugs bonded to high-molecular compounds as carriers capable of migrating into target organs have been studied in order to obtain the aimed pharmaceutical effect of the drugs on the target organs and to reduce the side effects of the drugs on the other organs.

For example, it is disclosed that drug delivery systems into liver comprising of drugs modified with the compounds obtained by combination of galactose and proteins or high-molecule compounds based on the fact that the receptors specific for galactose exist in liver parenchymal cell in High-Molecule Vol. 46, No. 11, 843–848 (1997).

In addition, it is disclosed that poly-L-glutamic acid derivatives wherein a part of or all of the consisting peptide bonds in the poly-L-glutamic acid of the formula

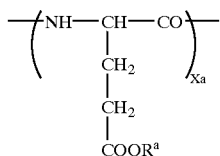

(wherein, Xa is degree of polymerization of 20~540, $R^a$ is hydrogen, lower alkyl or benzyl.) are replaced with a group of the formula

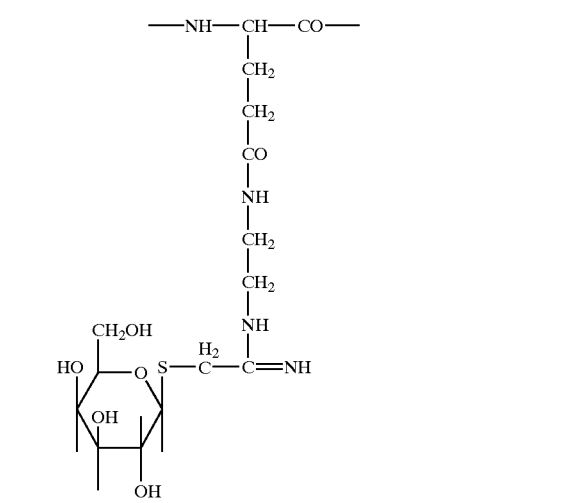

is useful as a carrier of drugs capable of migrating into liver in the Japanese Patent Application Kokai Hei 7-228688. The drugs have been conjugated to carboxyl group in the said glutamic acid via amide bond, ester bond or ion bond etc. directly. Vitamin K5 is described as an example of drugs in this publication.

Further, it is disclosed that polymers of $PGE_1$-containing L-glutamic acid derivative (abbreviated as polymer PA) of the formula

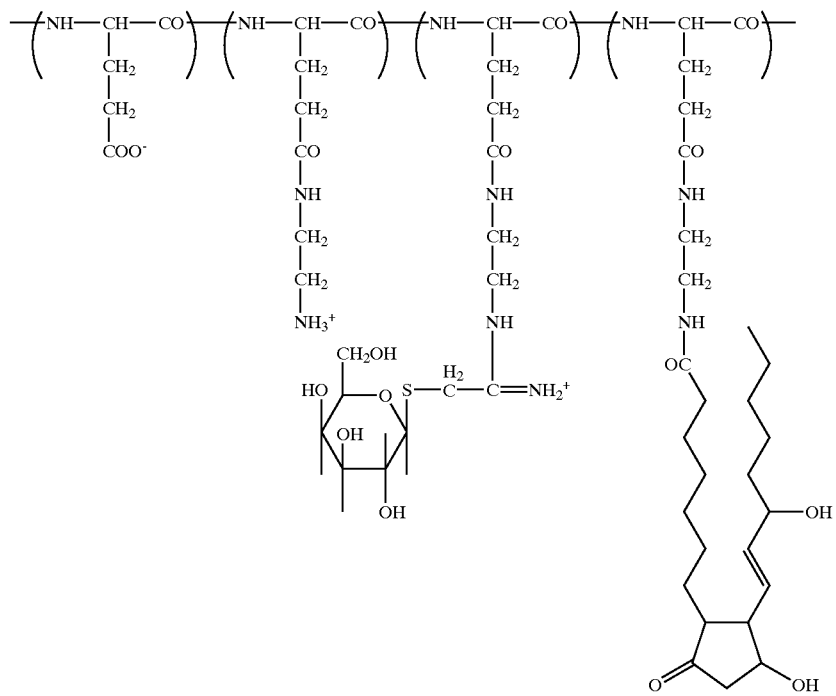

is as high-molecule prodrug of $PGE_1$ capable of migrating into liver in International. J. Pharmaceutics, 155, 65–74 (1997). The drug ($PGE_1$) is conjugated to L-glutamic acid via amide bond through ethylenediamine (—NH—$CH_2CH_2$—NH—) as a spacer.

In the process for the preparation of the said polymer PA, which comprises amidation by condensation between $PGE_1$ and ethylenediamine as a spacer (reacting the activated ester of $PGE_1$ with ethylenediamine using carbodiimide (CDI) etc.), the reaction was carried out in an alkaline condition. Therefore, there is a problem that the drug which is unstable in an alkaline condition (e.g. $PGE_1$) would be decomposed and that the introducing rate of drugs into poly-L-glutamic acid does not increase. In this publication, quantity of drugs ($PGE_1$) introduced into one molecule of polymer (degree of polymerization of L-glutamic acid=101) is 1.6 molecule.

The present inventors have dissolved such a problem by using hydrazine (—NH—NH—) instead of ethylenediamine (—NH—$CH_2CH_2$—NH—) as a spacer in the reaction of drugs (e.g. $PGE_1$) and L-glutamic acid. That is to say, the reaction to introduce the drugs ($PGE_1$) is carried out in a weak acidic condition, so it is possible to introduce the drugs constantly, even if it is unstable in an alkaline condition. Based on this reaction, they have improved the introducing rate of drugs (e.g. $PGE_1$) into poly-L-glutamic acid, and then succeeded in synthesis of drugs-containing polymers showing the superior effect. In addition, it has proved that any compounds can be introduced into the polymer constantly by using this reaction. For example, quantity of drugs ($PGE_1$) introduced into one molecule polymer of the present invention (degree of polymerization of L-glutamic acid=97) is 5 molecule, which means the polymer of the present invention has 3-folds superiority in introducing rate of drug to compare with the polymer of the said publication.

In addition, the polymer using hydrazine of the present invention shows superiority in both accumulation of drugs into liver after administration and effects of drugs (cytoprotective activity of $PGE_1$) to the polymers using ethylelendiamine.

Further, there is a merit that such a reaction between hydrazine and the drug ($PGE_1$) has been carried out by a simple procedure comprising of only stirring them at room temperature.

DISCLOSURE OF THE INVENTION

The present invention relates to (1) the polymer (abbreviated as Polymer P1.) wherein a part of or all of the consisting peptide bonds in the poly-L-glutamic acid of the formula (A)

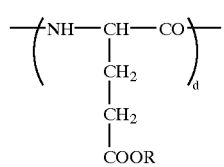
(A)

(wherein, degree of polymerization d is 20~500, R is hydrogen, C1~6 alkyl or benzyl, with the proviso that each multiple R may be same or different.)

are replaced with a group of the formula (i)
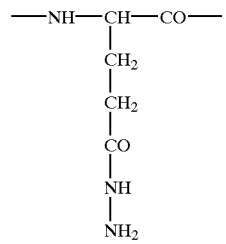
(B)

(ii)
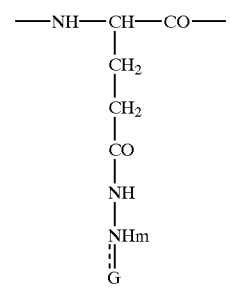
(C)

wherein

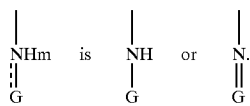

(wherein, G is a modified saccharide capable of conjugating to hydrazine))
as essential substituents with the proviso that when the number of replacement groups of the formula (C) is 2 or more, all of said groups are the same, (2) the polymer (abbreviated as Polymer P2) wherein a part of or all of the peptide bonds in the poly-L-glutamic acid of the formula (A)

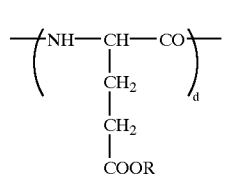
(A)

(wherein, all the symbols are defined as hereinbefore)

(i)
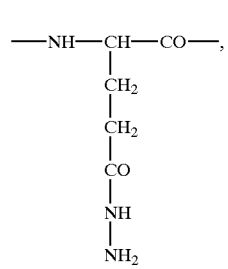
(B)

(ii)

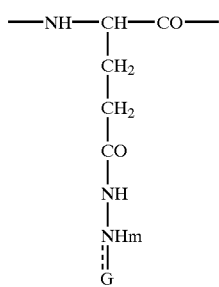

or (iii)

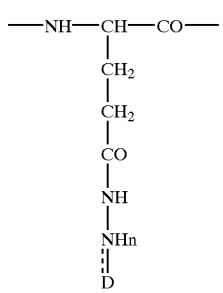

(wherein,

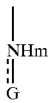
NHm
∥
G is defined as hereinbefore,

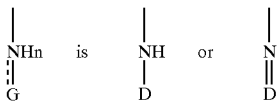

(wherein, D is a drug))
with the proviso that (1) groups of both the formula (C) and (D) are essential substituents, (2) when the number of replacement groups of the formula (C) or (D) is 2 or more, all of said groups of the formula (C) or (D) are the same and (3) the number of replacement groups of the formula (B) may be 0), and (3) the process for the preparation thereof.

DETAILED DESCRIPTION OF THE INVENTION

Polymer P1 is a carrier polymer capable of migrating into target organs (cells) and Polymer P2 is a drug-containing polymer, which is obtained by utilizing the said carrier polymer, capable of migrating into target organs (cells).

The delivery of the polymer of the present invention into target organs (cells) depends upon the saccharide (represented by G) conjugated to glutamic acid. It is known that various kinds of receptors for saccharides exist in organs (cells) and, new receptors may be found in the future study. It is possible to obtain the drug delivery system into target organs (cells) by choice of saccharide (G) capable of conjugating to the aimed organs (cells) including such known or new receptors.

For example, in case of monosaccharide, galactose receptor, mannose receptor and fucose receptor exist in liver parenchymal cells, liver nonparenchymal cells (endotherial cells and Kupffer cells) and Kupffer cells, respectively, so it is possible to obtain drug delivery system into liver (the said liver cells) by conjugate of galactose, mannose or fucose derivative (corresponds to Polymer P1 and P2 of the present invention in which

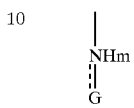

is a group of the formula of $(G^1)$, $(G^2)$ and $(G^3)$ described hereinafter.). For example, in case of oligosacchardies such as di, tri or tetrasaccharides etc. or multi-saccharides, the delivery of the polymer of the present invention into target organs (cells) depends upon the terminal saccharide. For example, the terminal saccharide of lactose which is one of disaccharide (corresponds to Polymer P1 and P2 of the present invention in which

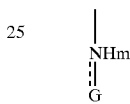

is a group of the formula $(G^{4a})$ and $(G^{5a})$.) is galactose, so such a polymer migrates into liver parenchymal cell mainly. As for the aimed saccharide, natural ones or artificial ones which are synthesized may be used.

The symbols and degree of polymerization etc. of Polymer P1 and P2 of the present invention are explained in detail as follows:

The symbol d in the formula (A) in Polymer P1 and P2 of the present invention means the degree of polymerization of L-glutamic acid which is a unit of the polymer of the present invention and it is an integer of 20~500, preferably 40~300 and more preferably 50~150.

The number of replacement of group of the formula (B) in Polymer P1 (corresponds to $y^2$ described hereinafter.) is 5~250 and preferably 5~50.

The number of replacement of group of the formula (C) (corresponds to $z^2$ described hereinafter.) is 10~100, and preferably 20~60.

The number of replacement of group of the formula (B) in Polymer P2 (corresponds to $y^3$ described hereinafter.) is 0~250, and preferably 0~50.

The number of replacement of group of the formula (C) (corresponds to $Z^3$ described hereinafter.) is 10~100, and preferably 20~60. The number of replacement of group of the formula (D) (corresponds to $W^3$ described hereinafter.) is 1~20, and preferably 1~10.

The average of molecule weight of Polymer P1 is 5,000~150,000. For example, the average of molecule weight of Polymer P1 using monosaccharide

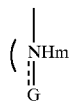

is a group of the formula $(G^1)$, $(G^2)$ and $(G^3)$ described hereinafter.) or disaccharide such as lactose derivative

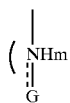

is a group of the formula ($G^{4a}$) and ($G^{5a}$) described hereinafter.) is 5,000~100,000 and preferably 10,000~30,000.

C1–6 alkyl in the formula (A) in Polymer P1 and P2 means methyl, ethyl, propyl, butyl, pentyl or hexyl or its isomer.

Each R is preferably, i) hydrogen or the said C1~6 alkyl (when multiple R are alkyl, they are the same.), ii) hydrogen or benzyl, or iii) hydrogen only, and more preferably, iii) hydrogen only.

The sacchardie represented by G in the formula (C) in Polymer P1 and P2 may be selected in accordance with the receptors which are know or may be found in the future study exist in the organs (cells), as mentioned before. The modified saccharides represented by G capable of conjugating to hydrazine include, for example, 2-iminoethyl-1-thiosaccharide derivatives and saccharides comprising a group wherein the linkage is cleaved etc.

The said 2-iminoethyl-1-thiosaccharide derivative represented by G include, for example, a group of the formula (if it is represented by

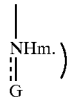

(i)

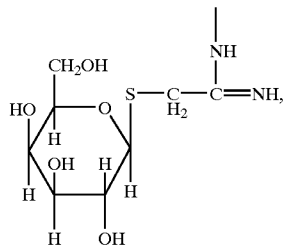

(ii)

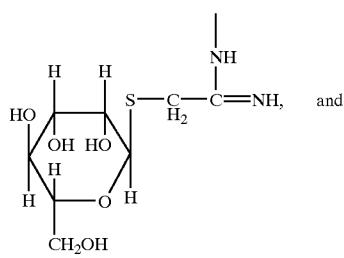

(iii)

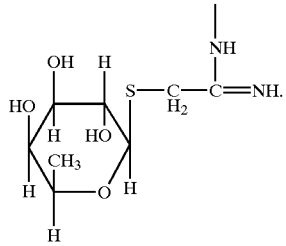

In addition, the said saccharide containing a group, wherein the linkage is cleaved, represented by G include, for example, group of the formula (if it is represented by

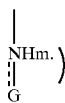

(iv)

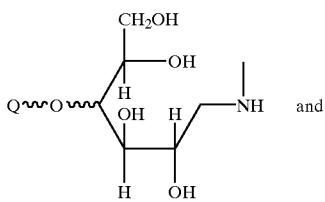
and (v)

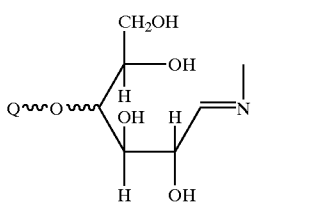

(wherein, Q is a saccharide chain containing 1~10 of saccharide.).

Further, 1~10 of saccharide represented by Q in the above formula include, for example, the saccharide of the formula

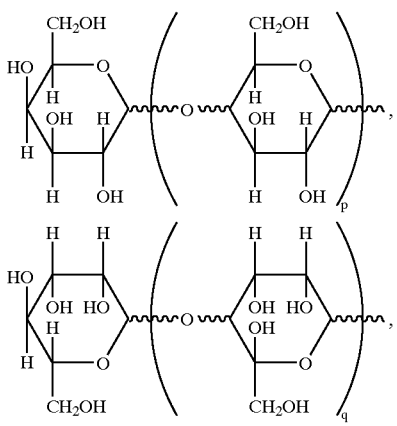

-continued

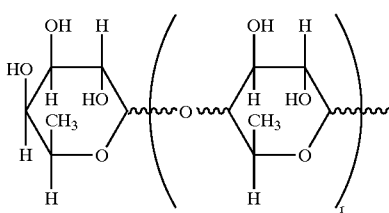

(wherein, each p, q and r is 0 or an integer of 1~9.), preferably galactose, mannose and fucose (corresponds to a group in which each p, q, r is 0 in the above formula) and more preferably galactose.

is preferably a group of the formula (i)

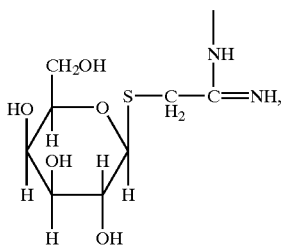
(G$^1$)

(ii)

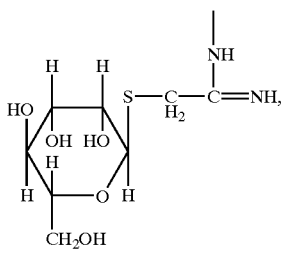
(G$^2$)

(iii)

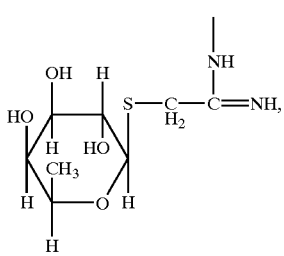
(G$^3$)

-continued (iv-1)

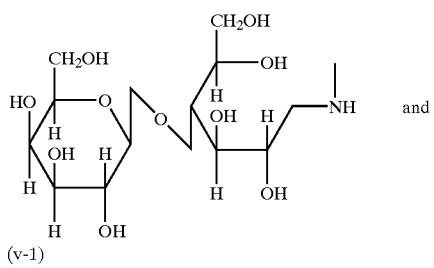
(G$^{4a}$)

and (v-1)

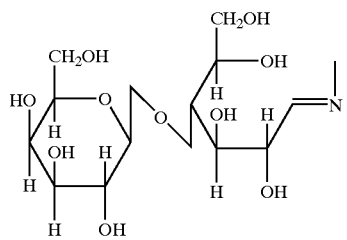
(G$^{5a}$)

and more preferably group of the formula (G$^1$), (G$^{4a}$) and (G$^{5a}$).

In Polymer P2, glutamic acid and drugs represented by D is conjugated via various kinds of bonds such as hydorazon bond or amide bond etc. through hydrazino (—NH—NH$_2$) which is introduced to L-glutamic acid in accordance with the structure of drugs.

The drugs represented by D included any drugs, and preferably, the drug which is unstable in an alkaline condition. Such an alkaline condition means pH8~11 preferably. Of course, it is possible to apply the drugs other than ones which are unstable in an alkaline condition.

Concrete drugs include PGs (e.g. PGEs, PGFs, PGDs), PGIs, naphthyloxyacetic acid derivatives, bicycloalkanoic acid derivatives, guanidinobenzoic acid derivatives, rhodanine acetic acid derivatives, cinnamoic acid derivatives, valproic acid derivatives, Vitamins, anti-allergic agents, anti-vital, anti-cancer agents etc.

PGs include natural PG such as PGE$_1$, PGE$_2$, PGF$_{1\alpha}$, PGF$_{2\alpha}$, PGD$_1$, PGD$_2$ etc. and its derivatives.

For example, natural PGE$_1$ and PGE$_2$ are the compounds shown by the following structures, respectively:

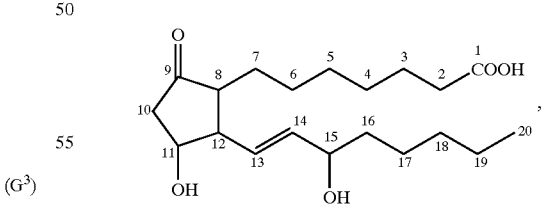
(PGE$_1$)

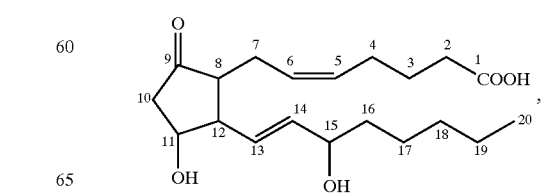
(PGE$_2$)

and $PGD_1$ and $PGD_2$ are the compounds shown by the following structures, respectively:

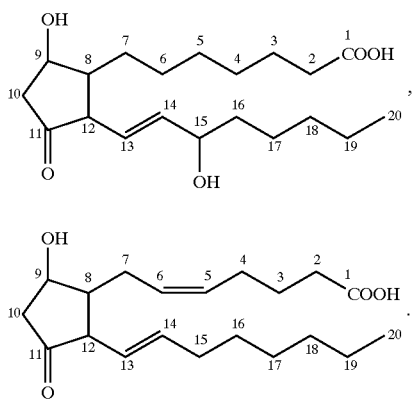

The concrete PGs include the compounds of the following formula

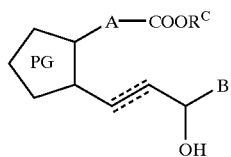

(wherein,

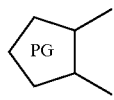

is

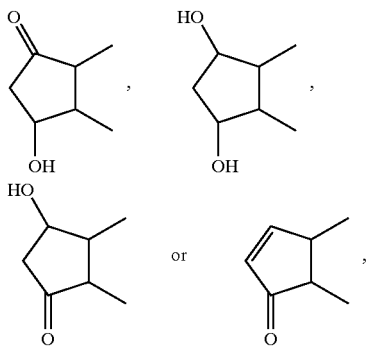

$R^c$ is hydrogen or various kinds of substituents of carboxyl group such as C1~12 alkyl, benzyl etc.,
A is C2~10 alkylene (1) in which optional carbon atom may be replaced with CO and/or (2) may have one or more double bond(s),
B is C1~10 alkyl, C2~10 alkenyl or C2~10 alkynyl may be substituted with phenyl, phenoxy or cycloalkyl (wherein each ring may be substituted with C1~6 alkyl, C2~6 alkenyl, C2~6 alkynyl, C1~6 alkoxy or halogen etc.),≡≡≡
is ethylene, trans-vinylene or ethynylene.).
PGs include preferably PGEs or PGDs (the compounds of the formula

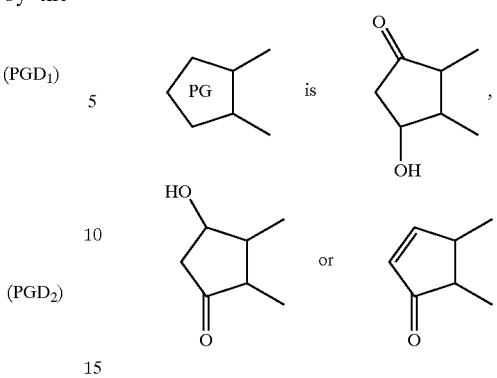

in the above formula), more preferably PGEs (the compounds of the formula

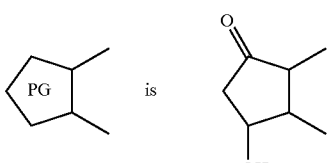

in the above formula).
Such compounds include
$PGE_1$, $PGE_2$, 17,20-dimethyl-trans-$\Delta^2$-$PGE_1$, 6-keto-17,20-dimethyl-trans-$\Delta^2$-$PGE_1$ methyl ester, 16,16-dimethyl-trans-$\Delta^2$-$PGE_1$ methyl ester etc.
PGEs and PGDs may be conjugated to L-glutamic acid via hydorazon bond at the 9th and 11th position carbon, respectively. For example, $PGE_1$ may be conjugated to L-glutamic acid as shown as following structure:

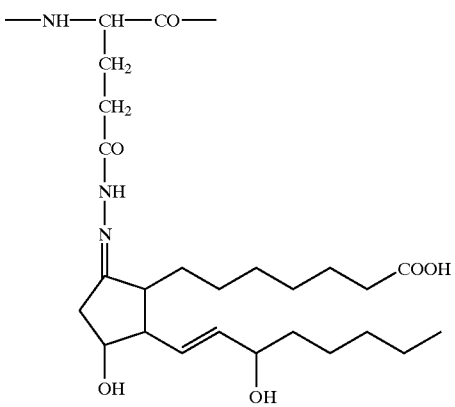

In addition, PGFs may be conjugated to L-glutamic acid via amide bond between the carboxyl group and amine group of hydrazine which is introduced.
PGIs include natural $PGI_2$ and its derivatives, for example, the compounds disclosed in Japanese Patent Application Kokai Sho 54-130543 and Sho 55-64541 (corresponding to GBP-2017699). PGIs may be conjugated to L-glutamic acid via amide bond.
Naphthyloxyacetic acid derivatives include, for example, the compounds disclosed in Japanese Patent Application Kokai Hei 6-87811 (corresponding to U.S. Pat. No. 5,480, 998), for example, [5-[2-[1-phenyl-(3-pyridyl) methylildenaminooxy]ethyl]-7,8-dihydronahthalene-1-yloxy]acetic acid shown by the formula

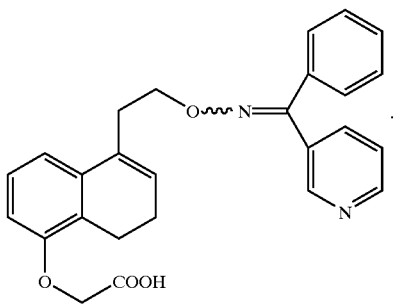

Such a naphthyloxyacetic acid compound may be conjugated to L-glutamic acid via amide bond at the terminal amino group of hydrazine as shown by the following structure:

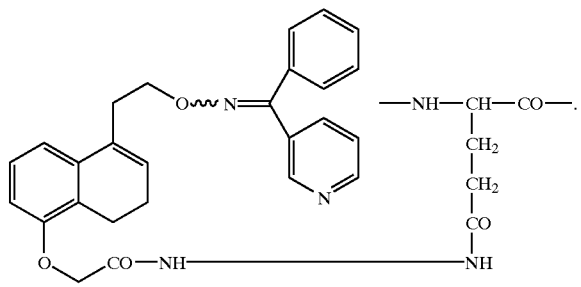

Bicycloalkanoic acid derivatives include, for example, the compounds disclosed in Japanese Patent Application Hei 9-140959 (corresponding to Japanese Patent Application Kokai Hei 11-29548).

Guanidinobenzoic acid derivatives include, for example, the compounds disclosed in Japanese Patent Application Kokai Sho 51-138642 (corresponding to U.S. Pat. No. 4,021,472).

Rhodanine acetic acid derivatives include, for example, the compounds disclosed in Japanese Patent Application Kokai Sho 57-40478 (corresponding to U.S. Pat. No. 4,464,382).

Cinnamoic acid derivatives include, for example, the compounds disclosed in 1) Japanese Patent Application Kokai Sho 55-313 (corresponding to U.S. Pat. No. 4,226,878), 2) Japanese Patent Application Kokai Sho 57-131769 (corresponding to U.S. Pat. No. 4,607,046) and 3) WO 98/27053.

Valproic acid derivatives include, for example, the compounds disclosed in Japanese Patent Application Kokai Hei 7-316092 (corresponding to EP-0632008A1).

[The Process for the Preparation of the Polymer of the Present Invention]

The polymer of the present invention may be prepared by the method described hereinafter in Examples, known methods or the method of the following reactions (1)–(3).

(1) introducing of hydrazine to poly-L-glutamic acid,
(2) introducing of saccharide (corresponds to G),
(3) introducing of drugs (corresponds to D).

In the reaction (1), poly-L-glutamic acid of the formula (A)

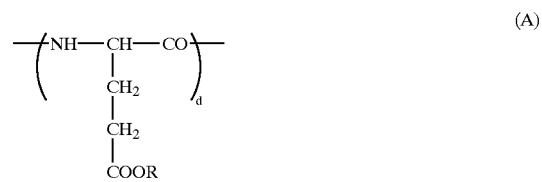

(wherein, all the symbols are defined as hereinbefore.)

is reacted with hydrazine shown by the formula $NH_2$—$NH_2$ in an organic solvent such as dimethylformadmide (DMF) etc. or without solvent at room temperature (10~25° C.) to prepare the polymer of the formula (II)

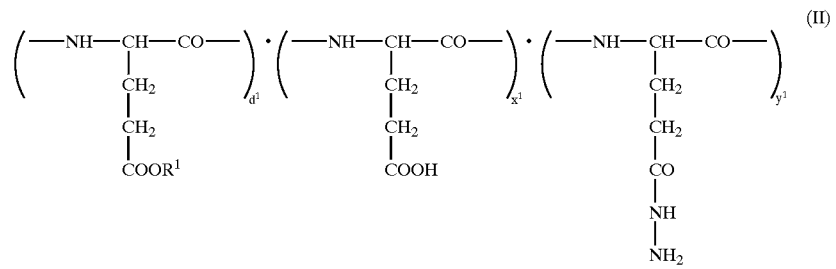

(wherein, $d^1$, $x^1$ and $y^1$ are mol (degree of polymerization) of L-glutamic acid connecting $COOR^1$ (wherein, $R^1$ is C1~6 alkyl or benzyl), L-glutamic acid connecting COOH and L-glutamic acid connecting $NH_2$, respectively. With the proviso that, (1) sum of $d^1$, $x^1$ and $y^1$ equals to d, (2) $d^1$ may be 0, (3) each L-glutamic acid connecting $COOR^1$ (wherein, $R^1$ is defined as hereinbefore.), COOH and $NH_2$ may be bonded at random in order.) (see the method described in J. Appl. Biochem., 2: 25 (1980)).

In the reaction (2), for example, saccharide (G) may be conjugated to hydrazine in the polymer of the formula (II) described hereinafter (a) by reacting the polymer of the formula (II)

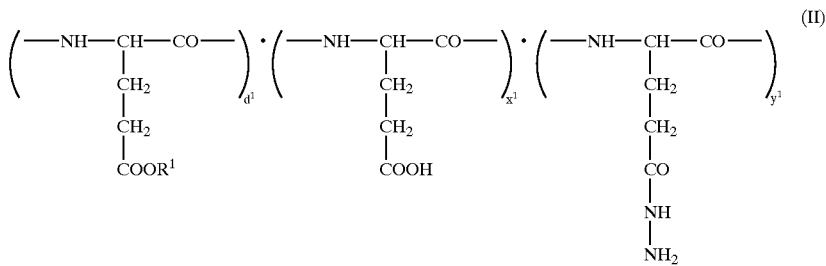

(wherein, all the symbols are defined as hereinbefore.)

and 2-imino-2-methoxyethyl-1-thiosaccharide in a weak alkaline condition (e.g. in borate buffer solution (pH9~10)) or (b) by reacting the polymer of the formula (II) and various kinds of saccharides, and then followed by reduction, if optionally.

2-Imino-2-methoxyethyl-1-thiosaccharide which is the starting material in the reaction (a) include, for example, 2-imino-2-methoxyethyl-1-thiogalactoside, 2-imino-2-methoxyethyl-1-thiomanoside or 2-imino-2-methoxyethyl-1-thiofucoside of the formula

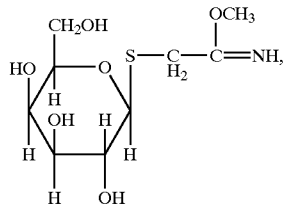

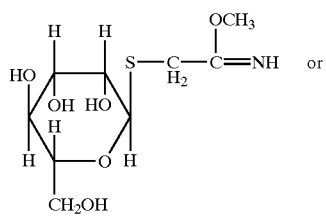

or

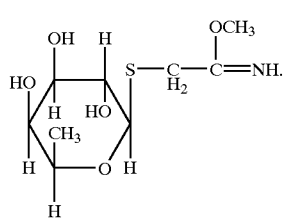

2-Imino-2-methoxyethyl-1-thiosaccharide is known compound or may be prepared by reacting cyanomethyl-1-thiosaccharide and sodium methoxide in methanol at room temperature (10~25° C.). (see the method described in Biochemistry Vol.15, No.18, 3956–3962 (1976)).

The saccharide which is starting material in reaction (b) include, for example, the compound of the formula

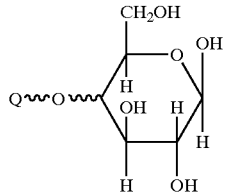

(wherein, Q is defined as hereinbefore.).

The polymer of the present invention wherein the formula

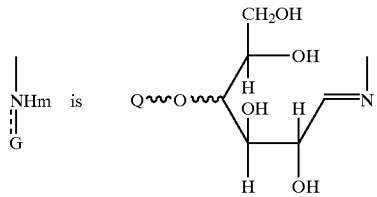

(wherein, Q is defined as hereinbefore.)

may be prepared by reacting aldehyde at the reductive terminal group of glucose of the saccharide which is used in the reaction and hydrazine in the polymer of the formula (II). This reaction is carried out in a weak acidic condition (e.g. in citrate buffer solution (pH4~6)) at room temperature (10~25° C.).

And then, the polymer of the present invention wherein the formula

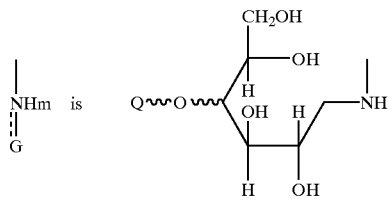

(wherein, Q is defined as hereinbefore.)

may be prepared by reduction, if optionally.

This reduction is called as reductive amidation. It may be carried out using reductive agent such as sodium borohydride, sodium cyanoborohydride etc. in a weak alkaline condition (e.g. in borate buffer solution (pH8~9)), at 30~50° C. By the same procedure, an ordinal saccharide may be conjugated to hydrazine.

By the known reaction other than the above (a) and (b), saccharide (G) may be conjugated to hydrazine in the polymer of the formula (II).

By the series of the above reactions, the polymer of the present invention (corresponds to the said polymer P1) of the formula (I-1)

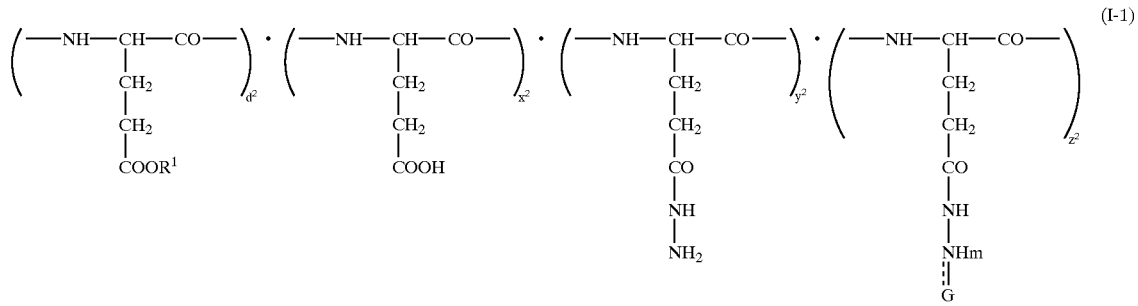

(wherein, $d^2$, $x^2$, $y^2$ and $z^2$ are mol (degree of polymerization) of L-glutamic acid connecting $COOR^1$ (wherein, $R^1$ is defined as hereinbefore.), L-glutamic acid connecting COOH, L-glutamic acid connecting $NH_2$ and L-glutamic acid connecting G (saccharide), respectively.

With the proviso that (1) sum of $d^2$, $x^2$, $y^2$ and $z^2$ equals to d, (2) $d^2$ may be 0, (3) each L-glutamic acid connecting $COOR^1$ (wherein, $R^1$ is defined as hereinbefore), L-glutamic acid COOH, L-glutamic acid $NH_2$ and L-glutamic acid G (saccharide) may be connected at random in order.) may be prepared.

In reaction (3), various kinds of reactions will be carried out in accordance with the structure of drugs.

1) Drugs possessing keto group (—CO—) may be conjugated via hydorazon bond which is formed by dehydro-condensation reaction with hydrazine in the polymer of the formula (I-1). This reaction is carried out in a weak acidic condition (e.g. in citrate buffer solution (pH4~6)), at room temperature (10~25° C.).
2) Drugs possessing carboxyl group (—COOH) may be conjugated via amide bond which is formed by amidation with amino group at the terminal of hydrazine in the polymer of the formula (I-1). This reaction is well known, it may be carried out, for example,
(1) by the method with using acid halide,
(2) by the method with using mixed acid anhydride,
(3) by the method with using conducing agent (EDC and DCC etc.).
3) Besides the above, drugs may be introduced to poly-L-glutamic acid via various kinds of bonds by known method.

And then, $NH_2$ in hydrazine in the group may be capped with saccharide by reacting the polymer prepared in reaction (3) and the same saccharide as introduced in the reaction (2) again, if optionally.

The drug-containing polymer of the present invention (corresponds to Polymer P2) of the formula (I-2)

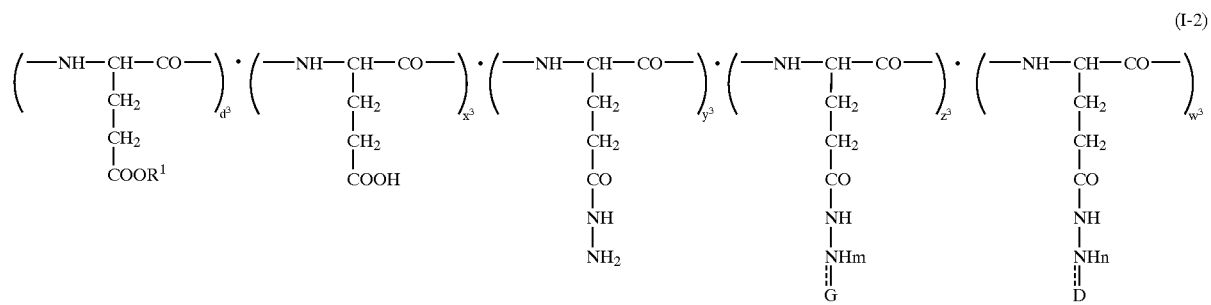

(wherein, $d^3$, $x^3$, $y^3$, $z^3$ and $w^3$ are mol (degree of polymerization) of L-glutamic acid connecting $COOR^1$ (wherein, $R^1$ is defined as hereinbefore.), L-glutamic acid connecting COOH, L-glutamic acid connecting $NH_2$, L-glutamic acid connecting G (saccharide) and L-glutamic acid connecting D(drug). With the proviso that (1) the sum of $d^3$, $x^3$, $y^3$, $z^3$ and $w^3$ equals to d, (2) $d^3$ and $y^3$, independently, may be 0, (3) L-glutamic acid connecting $COOR^1$ (wherein, $R^1$ is defined as hereinbefore.), COOH, $NH_2$, G (saccharide) and D (drug) may be conjugated at random in order.) may be prepared by series of these reactions.

In each reaction in the present specification, obtained products may be purified by conventional techniques. For example, purification may be carried out by distillation at atmospheric or reduced pressure, by high performance liquid chromatography, by thin layer chromatography or by column chromatography using silica gel or magnesium silicate, by washing or by recrystallization. Purification may be carried out after each reaction, or after a series of reactions.

[Starting Materials and Reagents]

The starting materials and reagents in the present invention are known per se or may be prepared by known methods.

Industrial Applicability

It has been confirmed that the polymer of the present invention represented as Polymer P1 possesses capability of migrating into target organs as shown hereinafter in Experiment. It is expected that the said polymer is decomposable in natural condition and that it is safe one, because it is natural high molecule compound. Therefore, the said polymer is useful as a carrier.

In addition, it has been confirmed that the drug-containing polymer of the present invention represented as Polymer P2 also possesses capability of migrating into target organs and superior effect as shown hereinafter in Experiments.

BEST MODE FOR CARRYING OUT THE INVENTION

The following abbreviations in Experiments and Examples mean as follows:
PLGA: poly-L-glutamic acid,
HZ: hydrazine,
ED: ethylenediamine,
[$^3$H]PGE$_1$-:
  PGE$_1$ bonded to hydrazine or ethylenediamine wherein the said
  PGE$_1$ is labeled with $^3$H partially,
Gal: 1-thiogalactpyranosyl-2-imino-ethyl,
-HZ-Lac (reductive): a group of the formula

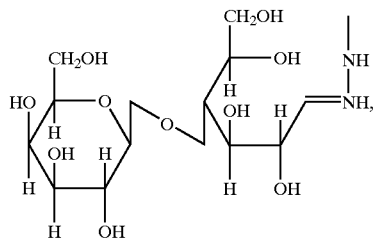

DMF: dimethylformamide,
MeOH: methanol,
MeONa: sodium methoxide,
EtOH: ethanol.

Experiment 1: Biodistribution of the Carrier Polymer of the Present Invention (Polymer P1)

PLGA-HZ-Gal (prepared in Example 3) and PLGA-HZ-Lac (prepared in Example 5) were labeled with $^{111}$In and were injected into mouse through its tail vein at dose of 1 mg/kg to analyze biodistribution of them. The results are shown in Tables 1 and 2 (Each value in Tables means the percentage of concentration in 1 ml of plasma, the percentage of amount of accumulation in each organ and the percentage of urinary excretion of the said PLGA derivatives (mean±S.D.), respectively at various times after administration.).

TABLE 1

Biodistribution data of PLGA-HZ-Gal

|  | 1 min. | 5 min. | 10 min. | 60 min. |
|---|---|---|---|---|
| Plasma | 47.76 ± 4.87 | 11.86 ± 4.71 | 2.41 ± 0.29 | 0.98 ± 0.16 |
| Kidney | 3.38 ± 0.41 | 1.61 ± 0.47 | 0.75 ± 0.13 | 0.53 ± 0.17 |
| Spleen | 0.02 ± 0.05 | 0.20 ± 0.10 | 0.15 ± 0.04 | 0.08 ± 0.03 |
| Liver | 34.90 ± 0.12 | 64.80 ± 8.41 | 75.65 ± 3.12 | 67.40 ± 3.32 |
| Lung | 0.11 ± 0.03 | 0.12 ± 0.01 | 0.09 ± 0.01 | 0.06 ± 0.02 |
| Urine | 0.04 ± 0.06 | 3.06 ± 4.33 | 10.93 ± 1.14 | 15.30 ± 1.11 |

TABLE 2

Biodistribution data of PLGA-HZ-Lac (reductive)

|  | 1 min. | 5 min. | 10 min. | 60 min. |
|---|---|---|---|---|
| Plasma | 42.16 ± 0.56 | 17.11 ± 5.85 | 1.99 ± 2.10 | 0.06 ± 0.03 |
| Kidney | 4.49 ± 0.40 | 4.67 ± 1.15 | 2.30 ± 1.45 | 1.24 ± 0.15 |
| Spleen | 0.10 ± 0.01 | 0.21 ± 0.02 | 0.22 ± 0.07 | 0.19 ± 0.01 |
| Liver | 24.53 ± 4.35 | 44.16 ± 5.47 | 59.51 ± 4.56 | 56.47 ± 3.57 |
| Lung | 0.53 ± 0.10 | 0.36 ± 0.05 | 0.11 ± 0.05 | 0.03 ± 0.00 |
| Urine | 0.16 ± 0.13 | 5.46 ± 2.89 | 9.67 ± 3.00 | 0.91 ± 0.30 |

About 60% of PLGA-HZ-Gal which was administered was accumulated into liver at 10 min. after administration. The same level of accumulation of it was observed in liver at 60 min.

About 60% of PLGA-HZ-Lac which was administered was accumulated into liver at 10 min. after administration. The same level of accumulation of it was observed in liver at 60 min.

From the mentioned, it has proved that the carrier polymer of the present invention showed high level of accumulation and long-term accumulation of it in liver.

Experiment 2: Biodistribution of the Drug-containing Polymer of the Present Invention (Polymer P2)

Biodistribution of [$^3$H]PGE$_1$-HZ-PLGA-HZ-Gal (prepared in Example 4, degree of polymerization=97) and [$^3$H]PGE$_1$-ED-PLGA-ED-Gal (Comparison: the polymer described in International J. Pharmaceutics, 155, 65–74 (1997), degree of polymerization=101) was analyzed by the same procedure as described in Experiment 1. The results are shown in Tables 3 (Invention) and 4 (Comparison) (Each value in Tables means the percentage of concentration in 1 ml of plasma, the percentage of amount of accumulation in each organ and the percentage of urinary excretion of the said [$^3$H]PGE$_1$ derivatives (mean±S.D.), respectively at various times after administration.).

TABLE 3

Biodistribution data of [$^3$H]-PGE$_1$-HZ-PLGA-HZ-Gal

|  | 1 min. | 5 min. | 10 min. | 60 min. |
|---|---|---|---|---|
| Plasma | 14.33 ± 0.75 | 1.64 ± 0.51 | 0.40 ± 0.06 | 0.26 ± 0.07 |
| Kidney | 1.26 ± 0.23 | 1.23 ± 0.06 | 0.79 ± 0.14 | 0.64 ± 0.22 |
| Spleen | 1.11 ± 0.14 | 1.85 ± 0.10 | 1.24 ± 0.17 | 1.84 ± 0.16 |
| Liver | 54.42 ± 0.79 | 70.39 ± 3.51 | 80.54 ± 9.52 | 85.43 ± 3.78 |
| Lung | 1.88 ± 0.46 | 1.64 ± 0.56 | 1.00 ± 0.21 | 0.44 ± 0.18 |
| Urine | 0.00 ± 0.00 | 1.17 ± 1.01 | 1.79 ± 0.25 | 1.45 ± 0.83 |

TABLE 4

Biodistribution data of [$^3$H]-PGE$_1$-ED-PLGA-ED-Gal

|  | 1 min. | 5 min. | 10 min. | 60 min. |
|---|---|---|---|---|
| Plasma | 36.55 ± 1.63 | 6.33 ± 0.84 | 1.99 ± 0.42 | 0.00 ± 0.00 |
| Kidney | 9.58 ± 1.46 | 28.82 ± 2.82 | 33.25 ± 5.63 | 13.16 ± 1.32 |
| Spleen | 0.41 ± 0.06 | 0.37 ± 0.17 | 0.63 ± 0.27 | 1.02 ± 0.53 |
| Liver | 27.72 ± 3.81 | 41.16 ± 2.04 | 47.19 ± 1.03 | 45.12 ± 8.21 |
| Lung | 1.97 ± 0.85 | 1.40 ± 0.13 | 0.82 ± 0.33 | 0.69 ± 0.14 |
| Urine | 0.05 ± 0.05 | 3.77 ± 2.28 | 2.28 ± 1.61 | 6.56 ± 3.15 |

As shown in Table 3, 70% of drug which was administered was accumulated into liver at 5 min. after administration. In addition, 85% and 70% of drug were observed to be accumulated to liver at 1 hour and 24 hours after administration, respectively.

On the other hand, in Comparison (Table 4) group, 40% and 45% of drug which was administered were accumulated to liver at 5 min. and 1 hour after administration, respectively.

Therefore, it has proved that it is possible to deliver the drug at the higher concentration continuously into liver using the drug-containing polymer of the present invention.
Experiment 3: Effect of the Drug ($PGE_1$)-containing Polymer of the Present Invention (Polymer P2) on $CCl_4$ Induced Liver Damage A solution of 10% (v/v) of $CCl_4$ in sesame oil at dose of 10 ml/kg was administered into mouse abdominal cavity, and then drug (saline solution (Control), Free-$PGE_1$ (Comparison), drug ($PGE_1$)-containing polymer of the present invention $PGE_1$-HZ-PLGA-HZ-Lac (reductive) (prepared in Example 6)) were injected into mouse through its tail vein at the setting dose. After the mouse had been fasted for 18 hours (25° C., water was freely given), blood was collected to assay GPT level (IU/L) in plasma. The results are shown in Table 5.

TABLE 5

| | n (No. of animals) | GPT level |
|---|---|---|
| Control (saline solution/CCl4 (−)) | 3 | 12.68 ± 1.527 |
| Control (saline solution/CCl4 (+)) | 5 | 614.56 ± 250.3 |
| Free $PGE_1$ (0.065 mg/kg) | 5 | 660.89 ± 218.28 |
| $PGE_1$-HZ-PLGA-HZ-Lac (1 mg/kg) | 4 | 239.12 ± 77.482 |

As shown in Table 5, the drug ($PGE_1$)-containing polymer of the present invention showed inhibition effect on increasing GPT level in plasma of $CCl_4$ induced liver damage significantly to compare with the group consisting of saline solution (Control group). In addition, the inhibition rate of increasing GPT level in the Invention group was three-time superior to that in the group consisting of free $PGE_1$ at the corresponding dose.

REFERENCE EXAMPLE AND EXAMPLES

The following Reference Examples and Examples are intended to illustrate, but not limit, the present invention. Each number represented as $d^t$, $x^t$, $y^t$ (t=1, 2, 3), $z^u$ (u=2, 3), $w^3$ in the column of degree of polymerization means mol of L-glutamic acid connecting $COOR^1$ (wherein, $R^1$ is C1~6 alkyl, benzyl.), L-glutamic acid connecting COOH, L-glutamic acid connecting $NH_2$, L-glutamic acid connecting G (galactose form or lactose form) and L-glutamic acid connecting D ($PGE_1$) per 1 mol of polymer.

Reference Example 1
Synthesis of PLGA-HZ (Degree of Polymerization: $d^1=0$, $x^1=29$, $y^1=50$)

To γ-benzyl-poly-L-glutamic acid (MW: 17,300, degree of polymerization=79) (200 mg), solution of hydrazine.monohydrate (10 ml) in DMF (3 ml) was added at a dropwise with stirring. The mixture was reacted for 3 hours at room temperature. The reaction solution was dialyzed with dialysis tube (3,500 molecular weight cut-off) (When the inner solution of tube became to be gel, the solution was recovered to be homogenous condition by addition of an adequate quantity of conc. HCl.). Inner solution of tube was ultrafiltered (10,000 molecular weight cut-off), concentrated and freezed to dry to obtain the title compound having the following physical data.

It was confirmed that each benzyl group, which was a protecting group of glutamic acid, was removed entirely by NMR analysis. In addition, hydrazine residue was assayed by β-naphathoquinon-4-sulphonate method.

MW: 10,900; degree of polymerization: $d^1=0$, $x^1=29$, $y^1=50$.

Example 1
Synthesis of PLGA-HZ-Gal (Degree of Polymerization: $d^2=0$, $x^2=29$, $y^2=8$, $z^2=42$)

(1) To cyanomethyl 1-thiogalacoside (150 mg), MeONa/MeOH (3 ml) was added. The mixture was stirred for 24 hours. MeOH was distilled off under reduced pressure from the mixture.

(2) PLGA-HZ (prepared in Reference Example 1) (50 mg) was dissolved in 2N HCl (1 ml). The mixture was neutralized by addition of 2N NaOH. Borate buffer solution (50 mM, pH9.5)(3 ml) was added thereto. The solution was added to the residue obtained in (1). The mixture was stirred for 5 hours at room temperature. The reaction solution was dialyzed, concentrated and freezed to dry to obtain the title compound having the following physical data. In addition, Gal residue was assayed by sulphate-anthron method.

MW: 20,900; degree of polymerization: $d^2=0$, $x^2=29$, $y^2=8$, $z^2=42$.

Example 2
Synthesis of [$^3$H]$PGE_1$-HZ-PLGA-HZ-Gal (Degree of Polymerization: $d^3=0$, $x^3=29$, $y^3=7$, $z^3=42$, $w^3=1$)

(1) PLGA-HZ-Gal (prepared in Example 1) (22.5 mg) was dissolved in 0.1M acetate buffer solution (pH5.0) (1 ml).

(2) To a solution of iced $PGE_1$ (2.5 mg) in EtOH (0° C., 1 ml), a solution of [$^3$H]$PGE_1$ (EtOH: $H_2O$=7:3; 0.5 μCi/ml) (0.1 ml) was added.

(3) Stirring the solution prepared in the above (1) at room temperature, the solution obtained in the above (2) was added at a dropwise thereto. 0.1M acetate buffer solution (pH5.0) (0.5 ml) was added thereto to clarify the solution. The solution was stirred for 24 hours at 4° C. After removing the impurities from the reaction mixture, the solution was dialyzed. The dialyzed solution was ultrafiltered (10,000 molecular weight cut-off, concentrated and freezed to dry to obtain the title compound having the following physical data.

MW: 21,200; degree of polymerization: $d^3=0$, $x^3=29$, $y^3=7$, $z^3=42$, $w^3=1$.

Example 3
Synthesis of PLGA-HZ-Gal (Degree of Polymerization: $d^2=0$, $x^2=29$, $y^2=37$, $z^2=31$)

By the same procedure as Reference Example 1→Example 1, the title compound having the following physical data was obtained using γ-benzyl-poly-L-glutamic acid (degree of polymerization=97).

MW: 20,800; degree of polymerization: $d^2=0$, $x^2=29$, $y^2=37$, $z^2=31$.

Example 4
Synthesis of $PGE_1$-HZ-PLGA-HZ-Gal and [$^3$H]$PGE_1$-HZ-PLGA-HZ-Gal (Degree of Polymerization: $d^3=0$, $x^3=29$, $y^3=32$, $z^3=31$, $w^3=5$)

PLGA-HZ-Gal (prepared in Example 3) (20 mg) was dissolved in 0.01M acetate buffer solution (pH5.0) (5 ml). Stirring this solution, a solution of $PGE_1$ (4 mg) in EtOH (0.5 ml) was added at a dropwise thereto. The mixture was stirred over night at room temperature. The reaction solution was dialyzed by saline solution to obtain the title compound (PGE$_1$-HZ-PLGA-HZ-Gal) having the following physical data. In addition, by the same procedure, the title compound ([$^3$H]PGE$_1$) having the following same physical data was obtained by addition of [$^3$H]PGE$_1$(10 μCi) to the said solution of PGE$_1$ in EtOH. Both compounds were stored as a solution form.

MW: 23,000; degree of polymerization: $d^3$=0, $x^3$=29, $y^3$=32, $z^3$=31, $w^3$=5.

Example 5

Synthesis of PLGA-HZ-Lac (Reductive/degree of Polymerization: $d^2$=0, $x^2$=35, $y^2$=40, $z^2$=22)

PLGA-HZ (MW: 13,300, degree of polymerization: $d^1$=0, $x^1$=35, $y^1$=62) (50 mg) which was prepared by the same procedure as Reference Example 1 using γ-benzyl-poly-L-glutamic acid (degree of polymerization=97) was dissolved in 5N NaOH and neutralized to about pH7 by addition of 5N HCl. 0.1M borate buffer solution (pH8.5) was added thereto to become to pH8~9. Lactose (143 mg) and sodium cyanoborohydride (50 mg) was added thereto. The solution was reacted for one day at 37° C. The reaction solution was purified with dialysis and freezed to dry to obtain the title compound having the following physical data.

MW: 20,800; degree of polymerization: $d^2$=0, $x^2$=35, $y^2$=40, $z^2$=22.

Example 6

Synthesis of PGE$_1$-HZ-PLGA-HZ-Lac (Reductive/degree of Polymerization: $d^3$=0, $x^3$=35, $y^3$=36, $z^3$=22, $w^3$=4)

By the same procedure as Example 2, the title compound having the following physical data was obtained using PLGA-HZ-Lac (reductive/prepared in Example 5).

MW: 22,800; degree of polymerization: $d^3$=0, $x^3$=35, $y^3$=36, $z^3$=22, $w^3$=4.

What is claimed is:

1. A polymer of the formula (A-1):

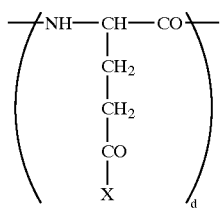

(A-1)

wherein d is an integer of 20–500, each X is independently selected from the group consisting of —OR, —NH—NH$_2$ and

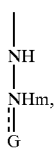

wherein each R is independently selected from the group consisting of hydrogen, C1–6 alkyl and benzyl, and wherein

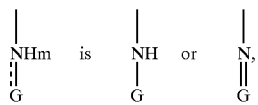

wherein G is a saccharide, with the proviso that (1) at least one X is —NH—NH$_2$ and at least one X is

and (2) when more than one X is

all of the

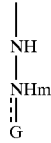

groups are the same.

2. A polymer according to claim 1, wherein

is (i)

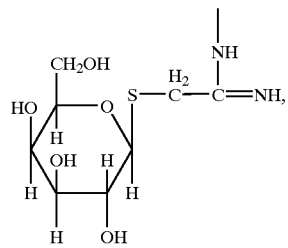

(G$^1$)

-continued
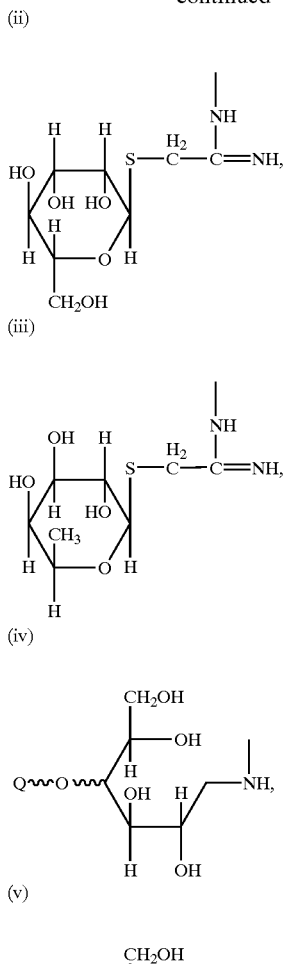
wherein, Q is a saccharide chain containing 1–10 saccharide subunits.
3. The polymer according to claim 1, wherein
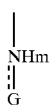
is
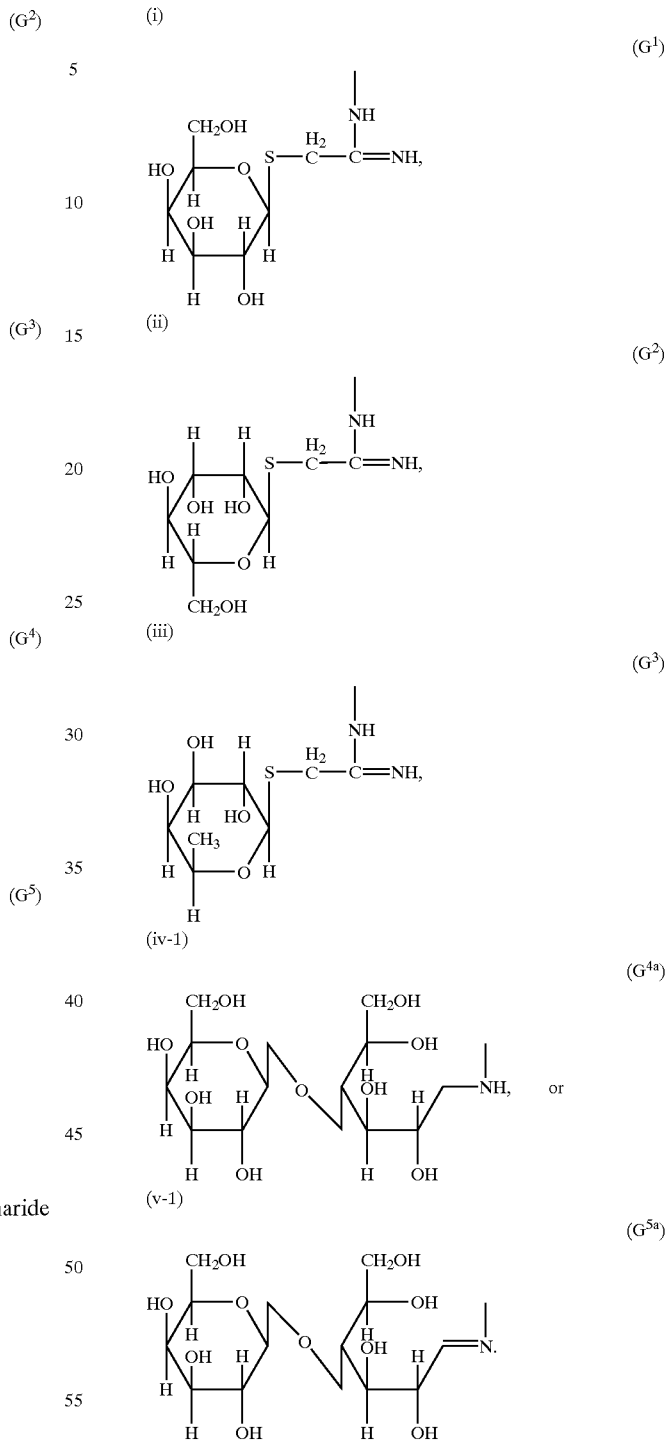
* * * * *